United States Patent
Suzuki et al.

(10) Patent No.: US 10,066,261 B2
(45) Date of Patent: Sep. 4, 2018

(54) METHOD FOR AMPLIFYING NUCLEIC ACID

(71) Applicants: SYSMEX CORPORATION, Kobe-shi, Hyogo (JP); NATIONAL UNIVERSITY CORPORATION NAGOYA UNIVERSITY, Nagoya-shi, Aichi (JP); Atsushi Maruyama, Yokohama-shi, Kanagawa (JP)

(72) Inventors: Seigo Suzuki, Kobe (JP); Hiroya Kirimura, Kobe (JP); Hiroyuki Asanuma, Nagoya (JP)

(73) Assignees: SYSMEX CORPORATION, Kobe-shi, Hyogo (JP); NATIONAL UNIVERSITY CORPORATION NAGOYA UNIVERSITY, Nagoya-shi, Aichi (JP); Atsushi Maruyama, Yokohama-shi, Kanagawa (JP)

(*) Notice: Subject to any disclaimer, the term of this patent is extended or adjusted under 35 U.S.C. 154(b) by 360 days.

(21) Appl. No.: 14/887,567

(22) Filed: Oct. 20, 2015

(65) Prior Publication Data

US 2016/0122809 A1 May 5, 2016

(30) Foreign Application Priority Data

Oct. 31, 2014 (JP) ................. 2014-223027

(51) Int. Cl.
  *C12Q 1/68* (2018.01)
  *C12Q 1/6853* (2018.01)
  *C12Q 1/6844* (2018.01)
  *C12Q 1/6848* (2018.01)

(52) U.S. Cl.
  CPC ......... *C12Q 1/6853* (2013.01); *C12Q 1/6844* (2013.01); *C12Q 1/6848* (2013.01)

(58) Field of Classification Search
  None
  See application file for complete search history.

(56) References Cited

U.S. PATENT DOCUMENTS

| 6,410,278 B1 | 6/2002 | Notomi et al. |
| 2012/0058518 A1 | 3/2012 | Yotoriyama |
| 2015/0093836 A1 | 4/2015 | Suzuki et al. |

FOREIGN PATENT DOCUMENTS

WO   01/21637 A1   3/2001

OTHER PUBLICATIONS

Extended European Search Report dated Mar. 11, 2016 issued from the European Patent Office in corresponding European Application No. 15192234.1.
Li et al., "Modification of Nucleic Acids by Azobenzene Derivatives and Their Applications in Biotechnology and Nanotechnology", Chem. Asian J., 2014, vol. 9, No. 12, pp. 3344-3358.
Kim et al., "DNA Strand Exchange Stimulated by Spontaneous Complex Formation with Cationic Comb-Type Copolymer", XP002904115, J. Am. Chem. Soc. 2002, vol. 124, No. 43, pp. 12676-12677.
Chang et al., "Diagnostic Devices for Isothermal Nucleic Acid Amplification", Sensors, 2012, vol. 12, No. 12, pp. 8319-8337.

*Primary Examiner* — Samuel C Woolwine
(74) *Attorney, Agent, or Firm* — Sughrue Mion, PLLC

(57) ABSTRACT

The present invention relates to a method for amplifying a nucleic acid. More specifically, the present invention relates to a method for amplifying a nucleic acid in a light irradiation dependent manner under a substantially isothermal condition using a photo-responsive nucleic acid.

19 Claims, 10 Drawing Sheets
Specification includes a Sequence Listing.

METHOD FOR AMPLIFYING NUCLEIC ACID

CROSS-REFERENCE TO RELATED APPLICATION

This application claims priority to Japanese patent application No. 2014-223027 filed on Oct. 31, 2014, which is incorporated herein by reference in its entirety.

BACKGROUND OF THE INVENTION

1. Technical Field

The present invention relates to a method for amplifying a nucleic acid.

2. Background

PCR (Polymerase chain reaction) is a most widely used and prevailing nucleic acid amplification method in various fields of research and medicine. In PCR, nucleic acids are amplified by repeating denaturation of double-stranded nucleic acids, elongation of strands from primers and the like by thermal cycles including repetition of heating and cooling of reaction mixtures. Recently, a nucleic acid amplification method has been developed which is carried out at a constant temperature (at approximately 60 to 70° C.) without thermal cycles. Such a method is represented by LAMP (Loop-mediated isothermal amplification) (see U.S. Pat. No. 6,410,278 which is incorporated herein by reference). In LAMP, the reaction is commenced by binding of a primer to a template nucleic acid under an isothermal condition. The reaction sequentially proceeds once the reaction is commenced, and thus the nucleic acid can be efficiently amplified. However, because of the nature of the isothermal amplification, strand displacement reaction develops sequentially without being able to be controlled once the reaction is commenced. Therefore it is difficult to address problems such as contamination during amplification reactions.

SUMMARY OF THE INVENTION

The scope of the present invention is defined solely by the appended claims, and is not affected to any degree by the statements within this summary.

The present invention provides a method for amplifying a nucleic acid, comprising the steps of:

irradiating a photo-responsive nucleic acid with light having a first wavelength to make the photo-responsive nucleic acid capable of associating with a first nucleic acid of a double stranded nucleic acid, wherein the double stranded nucleic acid comprises the first nucleic acid and a second nucleic acid, wherein the first nucleic acid is a single strand, and the second nucleic acid is a single strand and comprises a nucleotide sequence complementary to the first nucleic acid;

allowing complementary association of the photo-responsive nucleic acid with the first nucleic acid to dissociate the second nucleic acid from the first nucleic acid;

allowing complementary association of a first primer to the dissociated second nucleic acid; and extending a complementary strand from the first primer with a DNA polymerase, wherein the method is carried out under a substantially isothermal condition.

The present invention provides a method for amplifying a nucleic acid, comprising the steps of:

irradiating a photo-responsive nucleic acid with light having a first wavelength to make the photo-responsive nucleic acid capable of associating with a first nucleic acid of a double stranded nucleic acid, wherein the double stranded nucleic acid comprises the first nucleic acid and a second nucleic acid, wherein the first nucleic acid is a single strand, and the second nucleic acid is a single strand and comprises a nucleotide sequence complementary to the first nucleic acid;

allowing complementary association of the photo-responsive nucleic acid with the first nucleic acid to dissociate the second nucleic acid from the first nucleic acid;

irradiating the photo-responsive nucleic acid with light having a second wavelength that is different from the first wavelength to make the photo-responsive nucleic acid incapable of associating with the first nucleic acid;

allowing dissociation of the photo-responsive nucleic acid from the first nucleic acid;

allowing complementary association of a second primer to the dissociated first nucleic acid; and extending a complementary strand from the second primer with a DNA polymerase, wherein the method is carried out under a substantially isothermal condition.

The present invention provides a method for amplifying a nucleic acid, comprising the steps of:

irradiating a photo-responsive nucleic acid with light having a first wavelength to make the photo-responsive nucleic acid capable of associating with a first nucleic acid of a double stranded nucleic acid, wherein the double stranded nucleic acid comprises the first nucleic acid and a second nucleic acid, wherein the first nucleic acid is a single strand, and the second nucleic acid is a single strand and comprises a nucleotide sequence complementary to the first nucleic acid;

allowing complementary association of the photo-responsive nucleic acid with the first nucleic acid to dissociate the second nucleic acid from the first nucleic acid;

allowing complementary association of a first primer to the dissociated second nucleic acid;

extending a complementary strand from the first primer with a DNA polymerase, irradiating the photo-responsive nucleic acid with light having a second wavelength that is different from the first wavelength to make the photo-responsive nucleic acid incapable of associating with the first nucleic acid;

allowing dissociation of the photo-responsive nucleic acid from the first nucleic acid;

allowing complementary association of a second primer to the dissociated first nucleic acid; and extending a complementary strand from the second primer with a DNA polymerase, wherein the method is carried out under a substantially isothermal condition.

DETAILED DESCRIPTION OF THE EMBODIMENTS

Figure 1:
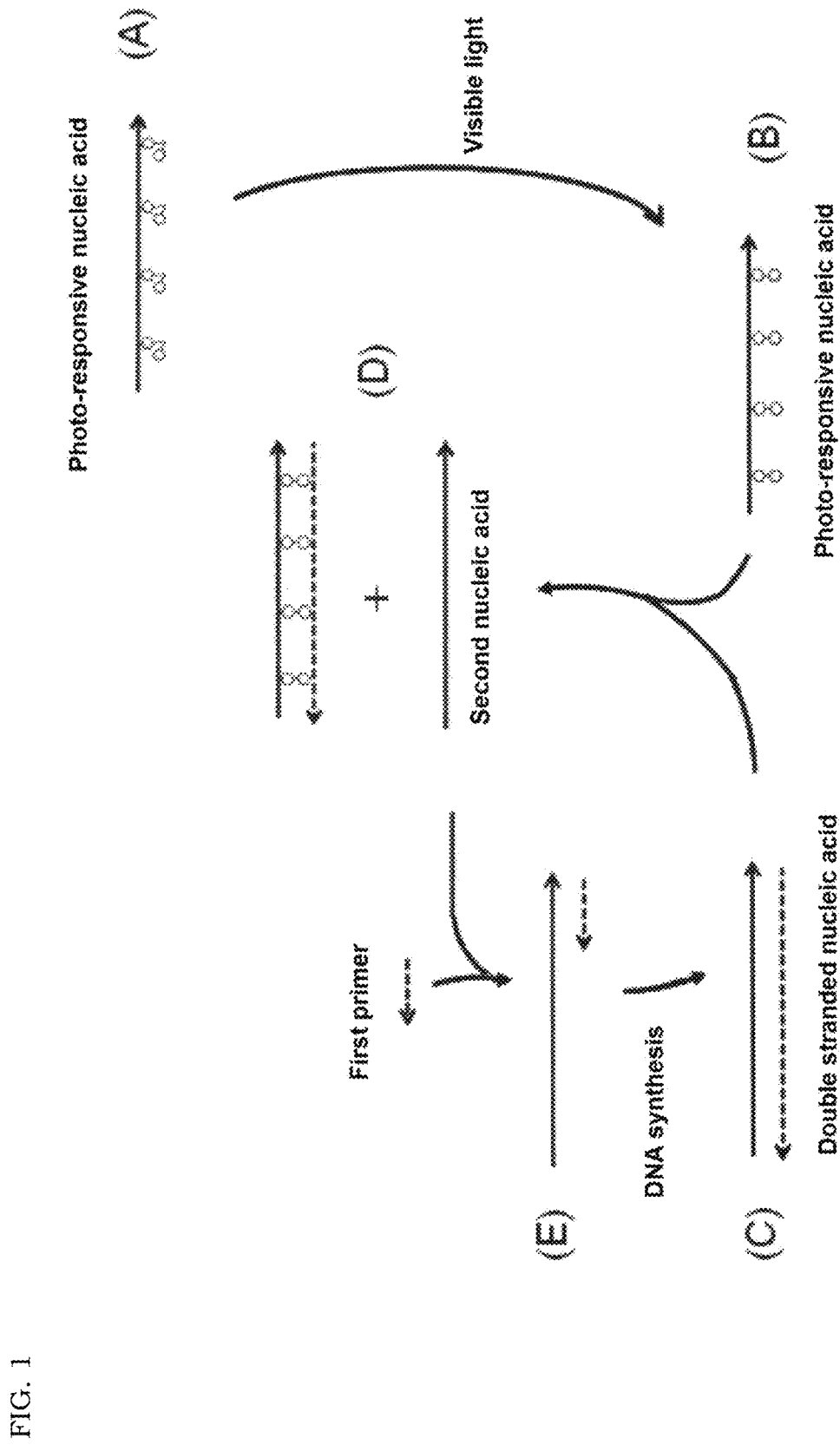
FIG. 1 is a conceptual diagram exemplifying a desirable reaction principle of embodiment 1.

The preferred embodiments of the present invention will be described hereinafter with reference to the drawings.

In a nucleic acid amplification method (hereinafter also merely referred to as "method") according to the present embodiment, a photo-responsive nucleic acid is used, thereby progress of amplification reaction of a double stranded nucleic acid can be controlled by light irradiation without thermal cycles such as those employed in PCR. Namely, the method according to the present embodiment does not require a step of heating for denaturing and dissociating a double stranded nucleic acid comprising a template nucleic acid and a complementary strand thereof or a step of cooling for associating a primer with the template nucleic acid. Thus the reaction system may be incubated at a substantially constant temperature. Thus the method according to the present embodiment can be carried out under a substantially isothermal condition. The temperature may be, for example, a temperature which is around a melting temperature (Tm) of a primer described hereinafter and which can maintain the activity of a DNA polymerase (45 to 70° C., preferably 55 to 65° C.).

The reaction system means a defined field or space where factors required for a nucleic acid amplification reaction exist and the reaction occurs. In the present embodiment, the reaction system may include, but is not limited to, for example a microdroplet such as a reaction solution or emulsion containing a double stranded nucleic acid, a photo-responsive nucleic acid, a primer, a DNA polymerase and a dNTP mixture (mixture of four dNTPs including dATP, dCTP, dGTP and dTTP) which is a substrate of the DNA polymerase and being accommodated in a container that allows transmission of light.

As used herein, the term "double stranded nucleic acid" refers to a nucleic acid comprising a first nucleic acid which is a single stranded nucleic acid and a second nucleic acid associated therewith by hydrogen bonding which is a single stranded nucleic acid complementary so as to be able to associate with the first nucleic acid. The "double stranded nucleic acid" also encompasses nucleic acids having a stem-loop structure. In this case, one strand in the "stem" portion which is a double stranded is designated as a first nucleic acid and the other strand is designated as a second nucleic acid.

As used herein, the expression "complementarily associate" or the like refers to the binding via a hydrogen bond of a whole or part of a polynucleotide to a whole or part of another polynucleotide under stringent conditions. In the present invention, "complementary association" and "hybridisation" are synonymous in terms of formation of a double strand via a hydrogen bond. The "stringent condition" may be a condition commonly used by a person skilled in the art during hybridisation of polynucleotides and may include the condition which allows specific hybridisation of a polynucleotide to the other polynucleotide, wherein the polynucleotides have at least 90% and preferably at least 95% sequence identity therebetween. Stringency of hybridisation is known to be a function of temperature, salt concentration, length and GC content of polynucleotides and concentration of a chaotropic agent in a hybridisation buffer. The stringent condition may be the one described in, for example, Sambrook, J. et al., 1998, Molecular Cloning: A Laboratory Manual (2nd edition), Cold Spring Harbor Laboratory Press, New York.

As used herein, the term "base sequence fully complementary to" or the like refers to a base sequence of a polynucleotide that forms complementary base pairs of Watson-Click model with all bases in the other polynucleotide.

An embodiment (embodiment 1) of the method according to the present embodiment, wherein a nucleic acid is amplified by using a second nucleic acid dissociated by means of a photo-responsive nucleic acid as a template is described hereinbelow. See FIG. 1 which exemplifies a desirable reaction principle of embodiment 1. FIG. 1 shows the principle of the reaction wherein a photo-responsive nucleic acid containing azobenzene attached thereto is used. In FIG. 1, a line with an arrow head represents a nucleic acid strand, wherein the arrow head represents 3' of the nucleic acid strand and the opposite side represents 5'. In FIG. 1, a dashed line represents a first nucleic acid in a double stranded nucleic acid and a solid line represents a second nucleic acid.

In the present embodiment, a step of irradiating a photo-responsive nucleic acid with light having a first wavelength to make the photo-responsive nucleic acid capable of associating with a first nucleic acid of a double stranded nucleic acid is first carried out. By referring to FIG. 1, in this step, a photo-responsive nucleic acid which is in the form incapable of associating with the first nucleic acid (see (A) in FIG. 1) is converted to the form capable of associating with the first nucleic acid by irradiation with visible light (see (B) in FIG. 1).

The double stranded nucleic acid which is to be amplified may be a double stranded DNA, a double stranded RNA or a hybrid of a single stranded RNA and a single stranded DNA. The morphology of the double stranded nucleic acid is not particularly limited and may be a cyclic double stranded nucleic acid such as a plasmid DNA or a hairpin-like double stranded nucleic acid which is a single stranded nucleic acid having a self-complementary region in the molecule. The origin of the double stranded nucleic acid is not particularly limited and may be a naturally-occurring double stranded nucleic acid such as genomic DNA or a double stranded nucleic acid (e.g., a mRNA-cDNA hybrid and a double stranded cDNA) synthesized or amplified from a naturally-occurring nucleic acid. The double stranded nucleic acid may, as far as it serves as a template for synthesis of a complementary strand, be modified with a well known label substance or contain an artificial derivative of a nucleotide substituting a nucleotide in the nucleic acid.

As used herein, the term "photo-responsive nucleic acid" refers to a single stranded nucleic acid containing one or more organic groups which undergo isomerization and conformational change by irradiation with light having a certain wavelength. Nucleic acids containing such organic groups per se are well known in the art and may include, for example, photo-responsive oligonucleotides described in WO 01/21637, which is incorporated herein by reference. In the present embodiment, complementary association with a first nucleic acid in a double stranded nucleic acid and dissociation from the associated strand can be reversibly carried out by utilizing the conformational change of the organic group in the photo-responsive nucleic acid by irradiation with light. The nucleic acid used for the photo-responsive nucleic acid may be DNA or RNA, or may be a conventionally well known artificial nucleic acid such as PS-oligo, PNA (peptide nucleic acid), morpholino oligo, 2'O-substituted RNA and BNA (Bridged Nucleic Acid), among which DNA is preferred.

The manner of binding of a nucleic acid to an organic group which may confer photo responsiveness to the nucleic acid (hereinafter also referred to as "photo-responsive organic group") in the photo-responsive nucleic acid is not particularly limited as far as the organic group binds to the nucleic acid so that the organic group forms a side chain of the nucleic acid. A side chain of a nucleic acid is a moiety corresponding to a base diverging from a pentose in a nucleotide constituting the nucleic acid. A backbone of a nucleic acid is a strand of nucleotides constituting the nucleic acid containing linkages between pentoses and phosphates. In the present embodiment, a photo-responsive organic group is regarded as being attached as a side moiety of a nucleic acid when the photo-responsive organic group binds to a 5'-terminal nucleotide or a 3'-terminal nucleotide of the nucleic acid. Examples of the manner of binding of a photo-responsive organic group to a nucleic acid may include direct binding of the organic group to a nucleotide so that the organic group is a side moiety of the nucleic acid or indirect binding of the organic group to the nucleic acid through an appropriate intervening group inserted into the backbone of the nucleic acid. The intervening group may be appropriately selected by a person skilled in the art and may include, for example, an alkylene group having 1 to 10, preferably 1 to 6 carbon atoms or a group containing an amino acid or a derivative thereof.

The photo-responsive organic group is suitably a group which can reversibly isomerise, by irradiation with light having a certain wavelength, from a substantially planar structure to a nonplanar structure. A compound that can be used as the organic group may include, for example, azobenzene, stilbene, spiropyran and derivatives thereof. It has been known that azobenzene and stilbene isomerise from trans forms to cis forms by irradiation with light. It has been known that spiropyran isomerises from a merocyanine form to a spiropyran form by irradiation with light.

In the present invention, the photo-responsive nucleic acid is preferably a nucleic acid containing a photo-responsive organic group that increases the melting temperature (Tm) of the nucleic acid compared to the Tm of a nucleic acid with an identical base sequence. Such a photo-responsive nucleic acid is suitably a nucleic acid containing at least one selected from the group consisting of azobenzene and a derivative thereof. The derivative of azobenzene is not particularly limited as far as it does not prevent formation of double strands and is particularly preferably dimethyl-azobenzene because it hardly undergoes isomerisation by heat. A nucleic acid containing azobenzene or a derivative thereof per se is well known in the art and can be commonly produced or is generally available.

Figure 2:
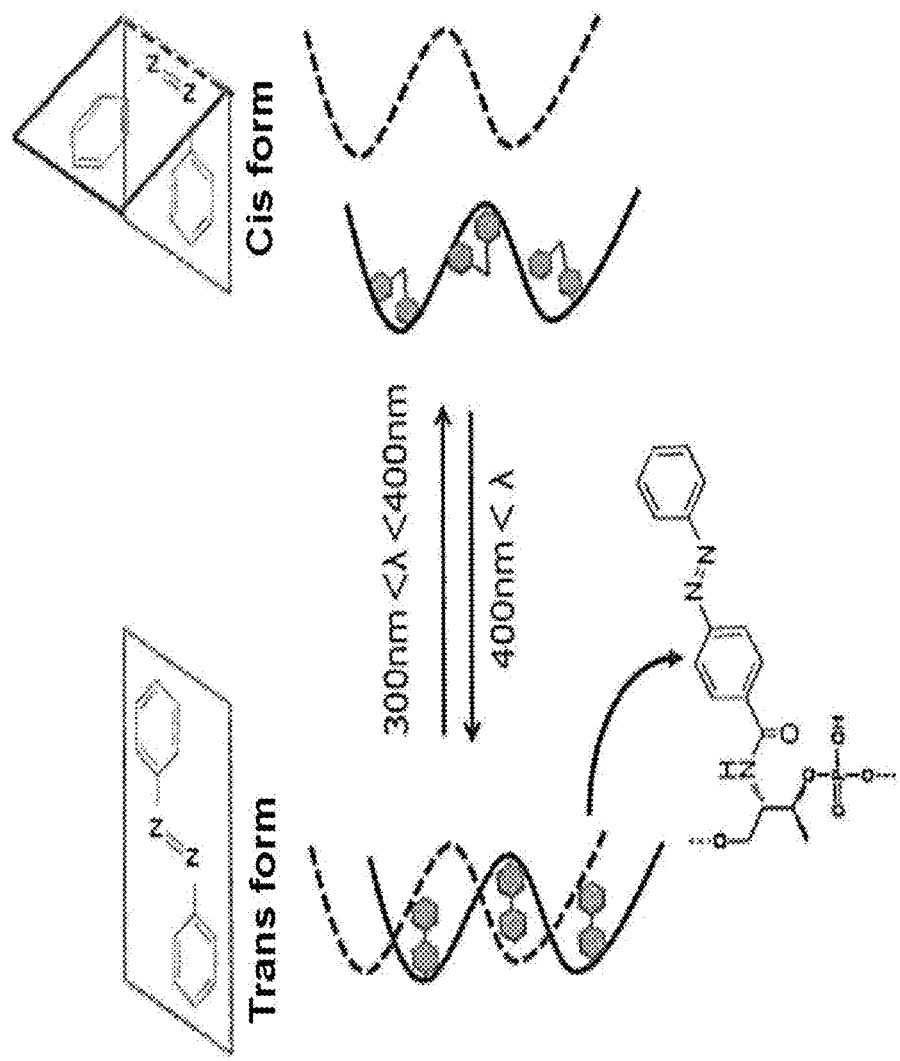
FIG. 2 is a conceptual diagram exemplifying photo-response of a photo-responsive nucleic acid containing azobenzene.

Azobenzene or a derivative thereof takes a planar trans form by irradiation with visible light having a wavelength of 400 nm or more and takes a three-dimensional cis form by irradiation with ultraviolet light having a wavelength of 300 to 400 nm. Thus by irradiation with visible light, azobenzene or a derivative thereof in the photo-responsive nucleic acid takes a planar trans form that does not prevent formation of double strands and thus the photo-responsive nucleic acid complementarily associates with a given nucleic acid strand to form a double strand. Meanwhile by irradiation with ultraviolet light, azobenzene or a derivative thereof in the photo-responsive nucleic acid takes a three-dimensional cis form, resulting in steric hindrance that prevents formation of a double strand. Due to this the photo-responsive nucleic acid is dissociated from the given nucleic acid in a double strand. See FIG. 2 which shows a model for formation and dissociation of a double stranded using a photo-responsive nucleic acid containing azobenzene or a derivative thereof. The photo-responsive nucleic acid shown in FIG. 2 contains azobenzene which is attached via D-threoninol inserted in the backbone of the nucleic acid so as to form a side chain moiety of the nucleic acid, which however does not limit the present invention.

When a photo-responsive nucleic acid containing azobenzene or a derivative thereof is used in the method of the present embodiment, the photo-responsive nucleic acid can take the form that is capable of associating with the first nucleic acid by irradiation with light having a first wavelength that is visible light having a wavelength of 400 nm or more.

The number of a photo-responsive organic group in a photo-responsive nucleic acid is not particularly limited as far as a double strand can be dissociated due to isomerisation. For example, one photo-responsive organic group may be introduced at every 2 to 10 bases in a photo-responsive nucleic acid.

When referring to a base sequence of a photo-responsive nucleic acid herein, a photo-responsive organic group attached to the nucleic acid may be disregarded and base portions of nucleotides are only looked at as a base sequence of general nucleic acids. For example, with regard to a photo-responsive nucleic acid containing a plurality of groups of azobenzene or a derivative thereof attached to a given single stranded nucleic acid, the base sequence of the photo-responsive nucleic acid is considered to be the same as that of the given single stranded nucleic acid.

The base sequence of the photo-responsive nucleic acid is not particularly limited as far as it allows complementary association with the first nucleic acid of the double stranded nucleic acid to be amplified. In the present embodiment, the photo-responsive nucleic acid preferably has a base sequence that is fully complementary to the base sequence of the first nucleic acid.

The photo-responsive nucleic acid may have any length as far as the nucleic acid can maintain complementary association with the first nucleic acid and is usually 10 to 100 nucleotides in length and preferably 15 to 50 nucleotides in length. In order to prevent the photo-responsive nucleic acid from providing a 3'-terminal that may serve as an origin of complementary strand synthesis, the photo-responsive nucleic acid may further comprise one to several bases attached to the 3'-terminal thereof that are not complementary to the first nucleic acid. More than one photo-responsive nucleic acid may be used.

In the method according to the present embodiment, regions in the double stranded nucleic acid with which a first primer and a second primer described hereinbelow can respectively associate vary depending on the base sequence and length of the photo-responsive nucleic acid. Thus it is preferable that the photo-responsive nucleic acid is designed according to a region for which amplification is sought in the double stranded nucleic acid.

In the present embodiment, the wavelength (first wavelength and second wavelength described hereinbelow) of light irradiated may be appropriately selected according to the type of the photo-responsive organic group. The period of irradiation of light may also be appropriately selected according to the type of the photo-responsive organic group and may be, in case of azobenzene, generally 1 to 300 seconds and preferably 15 to 60 seconds. In case of repeating the amplification reaction, light may be generally irradiated every 1 to 300 seconds, preferably every 15 to 60 seconds. The light source is not particularly limited as far as it can irradiate the reaction system with light having a predetermined wavelength and may include, for example, in case of azobenzene, a combination of a mercury lamp and a visible light filter or a LED having a predetermined wavelength.

In the present embodiment, a step of allowing complementary association of the photo-responsive nucleic acid which is capable of associating with a nucleic acid strand as described above with the first nucleic acid to dissociate the second nucleic acid from the first nucleic acid is carried out. By referring to FIG. 1, strand exchange between the double stranded nucleic acid (see (C) in FIG. 1) and the photo-responsive nucleic acid (see (B) in FIG. 1) allows formation of a double strand between the photo-responsive nucleic acid and the first nucleic acid and dissociation of the second nucleic acid from the first nucleic acid (see (D) in FIG. 1).

This step is desirably carried out under a situation that allows strand exchange of the second nucleic acid by the photo-responsive nucleic acid. This situation can be created by the condition under which both formation of hydrogen bonds and dissociation occur between base pairs in the double stranded nucleic acid. Specific examples of the condition may include, but are not limited to, an incubation of the reaction system at a temperature which is around Tm of a primer used and which can maintain the activity of a DNA polymerase (for example, 45 to 70° C., preferably 55 to 65° C.) or addition of a strand-exchange-enhancing substance described hereinafter to the reaction system. Under this condition, two nucleic acid strands in the double stranded nucleic acid dissociate and the photo-responsive nucleic acid can complementarily associate with the first nucleic acid of the double stranded nucleic acid due to the complementarity of the base sequences. Accordingly the second nucleic acid of the double stranded nucleic acid can be dissociated.

The length of the portion in the second nucleic acid that dissociates from the first nucleic acid depends on the length of the photo-responsive nucleic acid (more specifically, the length of the portion in the photo-responsive nucleic acid which complementarily associates with the first nucleic acid). Namely according to the present embodiment, when the photo-responsive nucleic acid has a length that is shorter than the double stranded nucleic acid, a part of the second nucleic acid is dissociated from the first nucleic acid. When the photo-responsive nucleic acid has a length that is longer than the double stranded nucleic acid, the whole second nucleic acid is dissociated.

In the present embodiment, in order to allow effective association of the photo-responsive nucleic acid with the first nucleic acid, it is preferable that the concentration of the photo-responsive nucleic acid is higher than the concentration of the double stranded nucleic acid at the beginning of amplification reaction. Specific concentrations of the nucleic acids may be appropriately selected by a person skilled in the art and it is particularly preferable that the concentration of the photo-responsive nucleic acid is 10 times or more higher than the concentration of the double stranded nucleic acid.

In order to allow effective association of the photo-responsive nucleic acid with the first nucleic acid, it is also advantageous to carry out the method according to the present embodiment under a high salt concentration condition. The salt is not particularly limited as far as it does not damage the nucleic acids and does not inhibit DNA polymerisation reaction. The salt may include, for example, NaCl, KCl and the like. The salt concentration is desirably within the range that can maintain complementary association between two nucleic acid strands and in which DNA polymerase is functional. When NaCl is used, the concentration may be up to 1 M.

In order to allow effective association of the photo-responsive nucleic acid with the first nucleic acid, it is also advantageous to carry out the method according to the present embodiment in the presence of a well known strand-exchange-enhancing substance. The strand-exchange-enhancing substance is well known in the art and may include, for example, at least one selected from the group consisting of a cationic homopolymer and a cationic copolymer. The cationic homopolymer and cationic copolymer may include, for example, homopolymers and copolymers derived from monomers that can form a cationic group such as amino acids including lysine, arginine and histidine, saccharides including glucosamine, synthetic monomers including ethyleneimine, diethylaminoethyl methacrylate, dimethylaminoethyl methacrylate and the like.

The cationic homopolymer or copolymer preferably has a graft structure containing a hydrophilic polymer modifying on a side chain. The side chain (grafted chain) is formed by, for example, at least one water-soluble polymer selected from the group consisting of water-soluble polyalkylene glycols such as polyethylene glycol; water-soluble polysaccharides such as dextran, pullulan, amylose and arabinogalactan; water-soluble polyamino acids containing hydrophilic amino acids such as serine, asparagine, glutamine and threonine; water-soluble polymers synthesized with monomers of acrylamide and a derivative thereof; water-soluble polymers synthesized with monomers of methacrylic acid, acrylic acid and a derivative thereof (e.g., hydroxyethyl methacrylate); polyvinyl alcohols and derivatives thereof. The molecular weight of the cationic homopolymer or copolymer and the chain length and degree of grafting of the side chain modification group are not particularly limited and may be appropriately selected by a person skilled in the art.

The strand-exchange-enhancing substance is particularly preferably a poly(L-lysine)-graft-dextran copolymer (PLL-g-Dex) which is a cationic copolymer. PLL-g-Dex per se is disclosed in Japanese Unexamined Patent Application Publication No. 2001-78769.

The concentration of the strand-exchange-enhancing substance in the reaction system is not particularly limited as far as nucleic acid amplification reaction is not inhibited and can be appropriately selected by a person skilled in the art.

In the present embodiment, a step of allowing complementary association of a first primer to the thus dissociated second nucleic acid of the double stranded nucleic acid is carried out. By referring to FIG. 1, in this step, association of the first primer to the dissociated second nucleic acid allows amplification reaction in which the second nucleic acid is used as a template (see (D) and (E) in FIG. 1).

The first primer is not particularly limited as far as it hybridises with the second nucleic acid under stringent conditions and can provide a 3'-terminal that serves as the origin of complementary strand synthesis. The first primer generally is 5 to 50 nucleotides in length and preferably 10 to 40 nucleotides in length. The first primer can be appropriately designed according to the base sequence of a nucleic acid strand to be amplified. The primer per se can be produced according to a nucleic acid synthesis method well known in the art.

In the present embodiment, the photo-responsive nucleic acid has a base sequence that can complementarily associate with the first nucleic acid and the first primer has a base sequence that can complementarily associate with the second nucleic acid. Therefore, the first primer may complementarily associate with the photo-responsive nucleic acid. In order to decrease the chance of complementary association of the first primer with the photo-responsive nucleic acid, the first primer may be designed so that the first primer has a portion, which complementarily associates with the second nucleic acid, having a length that is shorter than the length of the photo-responsive nucleic acid.

In the present embodiment, the primer may be labelled with a well known label substance. Optionally, the primer may comprise a functional oligonucleotide at the 5'-terminal thereof such as a recognition sequence of a certain restriction enzyme or a tag sequence.

In the present embodiment, a step of extending a complementary strand from the first primer associated with the dissociated second nucleic acid with a DNA polymerase is carried out. By referring to FIG. 1, in this step, the first primer is extended by a DNA polymerase with using the dissociated second nucleic acid as a template and a new double stranded nucleic acid is generated (see (E) and (C) in FIG. 1).

This step corresponds to the final step of the nucleic acid amplification reaction according to the present embodiment. When the reaction is not terminated, the double stranded nucleic acid generated in this step is subjected to the series of the steps described hereinabove, similarly to the double stranded nucleic acid which has originally been present in the reaction system, and the nucleic acid amplification reaction cycle is repeated.

DNA polymerase used in the present embodiment is not particularly limited as far as it has an activity to synthesize a complementary strand depending on the base sequence of a template nucleic acid and is particularly preferably a strand exchange DNA polymerase. In the method according to the present embodiment, when the photo-responsive nucleic acid has a length that is shorter than that of a double stranded nucleic acid to be amplified, the double stranded nucleic acid has a portion which is not dissociated. In this case, when a strand exchange DNA polymerase is used, the primer can be extended while dissociating the portion in the double stranded nucleic acid which has not been dissociated. Strand exchange DNA polymerase is well known in the art and is generally available. Strand exchange DNA polymerase may include, for example, Bst DNA polymerase, Aac DNA polymerase, Csa DNA polymerase, BcaBEST™ DNA polymerase, 96-7 polymerase and the like, among which Bst DNA polymerase is particularly preferable.

In the method according to the present embodiment, an additive for suitably carrying out the nucleic acid amplification reaction with a DNA polymerase may be added to the reaction system. The additive may include, for example, a buffer and a salt. The buffer is not particularly limited as far as it provides suitable pH for DNA polymerase and may include, for example, Tris-HCl, MES, phosphate buffers and the like. The salt may include, for example, NaCl, KCl, $(NH_4)_2SO_4$ and the like. Additives such as buffers and salts that are used for general nucleic acid amplification reaction are well known in the art and suitable additives according to the type of the DNA polymerase are generally available.

Figure 3:
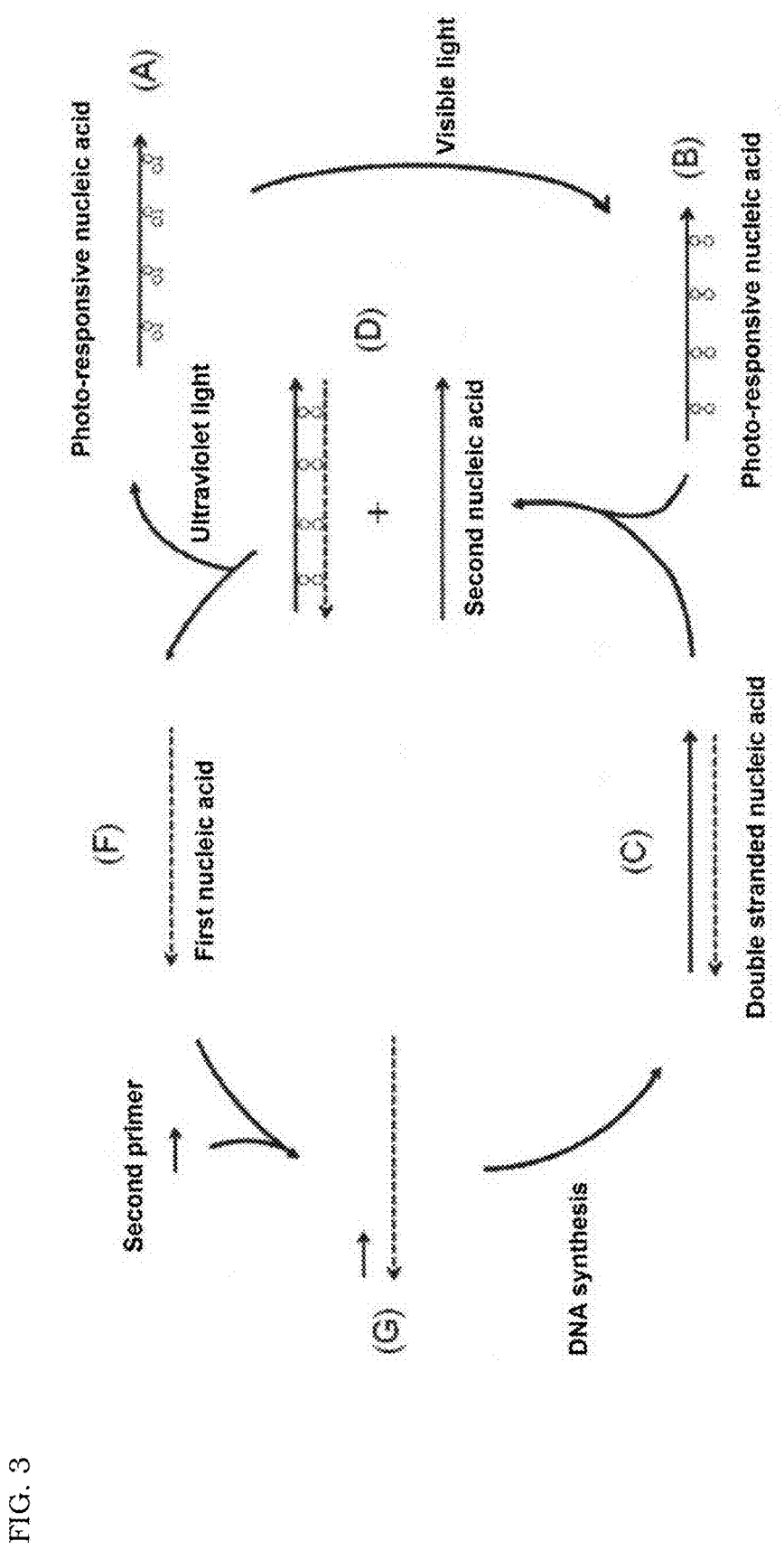
FIG. 3 is a conceptual diagram exemplifying a desirable reaction principle of embodiment 2.

An embodiment (embodiment 2) of the method according to the present embodiment, wherein a nucleic acid is amplified by using a first nucleic acid complementarily associated with a photo-responsive nucleic acid as a template is described hereinbelow. See FIG. 3 which exemplifies a desirable reaction principle of embodiment 2. FIG. 3 shows the principle of the reaction wherein a photo-responsive nucleic acid containing azobenzene attached thereto is used. In FIG. 3, a line with an arrow head represents a nucleic acid strand, wherein the arrow head represents 3' of the nucleic acid strand and the opposite side represents 5'. In FIG. 3, a dashed line represents a first nucleic acid in a double stranded nucleic acid and a solid line represents a second nucleic acid.

In the present embodiment, a step of irradiating a photo-responsive nucleic acid with light having a first wavelength to make the photo-responsive nucleic acid capable of associating with a first nucleic acid in a double stranded nucleic acid is first carried out (see (A) and (B) in FIG. 3). A step of allowing complementary association of the photo-responsive nucleic acid with the first nucleic acid to dissociate the second nucleic acid in the double stranded nucleic acid from the first nucleic acid is then carried out (see (B), (C) and (D) in FIG. 3). The details for the steps are the same as those described above for embodiment 1.

In the present embodiment, a step of irradiating the photo-responsive nucleic acid with light having a second wavelength to make the photo-responsive nucleic acid incapable of associating with the first nucleic acid is carried out (see (D) and (A) in FIG. 3).

The light having a second wavelength may be light that has a different wavelength from the light having a first wavelength used in the step of making the photo-responsive nucleic acid capable of associating with the first nucleic acid and that can sterically isomerise an organic group in the photo-responsive nucleic acid, so that the photo-responsive nucleic acid cannot associate with the nucleic acid strand. When the photo-responsive nucleic acid used contains azobenzene or a derivative thereof for example, irradiation with light having a second wavelength that is ultraviolet light having a wavelength of 300 to 400 nm can transform azobenzene to have a cis form, resulting in the photo-responsive nucleic acid incapable of associating with the first nucleic acid.

The interval between irradiation with light having a first wavelength and irradiation of light having a second wavelength may be appropriately selected without particular limitation and may be usually 1 to 300 seconds and preferably 15 to 60 seconds. The period of irradiation of light having a second wavelength may be appropriately selected according to the type of the organic group in the photo-responsive nucleic acid, and may be, in case of azobenzene, generally 1 to 300 seconds and preferably 5 to 60 seconds. In case of repeating amplification reaction, light having a first wavelength may be irradiated generally 1 to 300 seconds and preferably 5 to 60 seconds after irradiation of light having a second wavelength. The light source is not particularly limited as far as it can irradiate the reaction system with light having a predetermined wavelength and may include, for example, in case of azobenzene, a combination of a mercury lamp and an ultraviolet light filter or a LED having a predetermined wavelength.

In the present embodiment, a step of allowing dissociation of the first nucleic acid from the photo-responsive nucleic acid thus made incapable of associating with the nucleic acid strand is carried out. In this step, due to steric hindrance of the organic group in the photo-responsive nucleic acid, a hydrogen bond between a base in the photo-responsive nucleic acid and a base in the first nucleic acid cannot be maintained, resulting in dissociation of the photo-responsive nucleic acid from the first nucleic acid (see (D), (A) and (F) in FIG. 3).

In the present embodiment, a step of allowing complementary association of a second primer with the thus dissociated first nucleic acid is carried out. By referring to FIG. 3, in this step, association of a second primer to the dissociated first nucleic acid (see (F) in FIG. 3) allows amplification reaction in which the first nucleic acid is used as a template (see (G) in FIG. 3). The second primer is not particularly limited as far as it is an oligonucleotide that hybridises with the first nucleic acid under stringent conditions and can provide a 3'-terminal that serves as the origin of complementary strand synthesis. The length, base sequence, synthesis method, a label and the like for the second primer are similar to those described for the first primer.

In the present embodiment, a step of extending a complementary strand from the second primer associated with the first nucleic acid with a DNA polymerase is carried out. By referring to FIG. 3, in this step, the second primer is extended by a DNA polymerase by using the first nucleic acid as a template and a new double stranded nucleic acid is generated (see (G) and (C) in FIG. 3). DNA polymerase is as described for embodiment 1.

This step corresponds to the final step of the nucleic acid amplification reaction according to the present embodiment. When the reaction is not terminated, the double stranded nucleic acid generated in this step is subjected to the series of the steps described hereinabove, similarly to the double stranded nucleic acid which has originally been present in the reaction system, and the nucleic acid amplification reaction cycle is repeated.

In the present embodiment, a nucleic acid amplification method in which embodiment 1 and embodiment 2 are combined may be carried out. This corresponds to the embodiment in which a nucleic acid is amplified with a pair of primers consisting of the first primer and the second primer. This embodiment (embodiment 3) is described hereinbelow. See FIGS. 4 and 5 which exemplify desirable reaction principles of embodiment 3.

Figure 4:
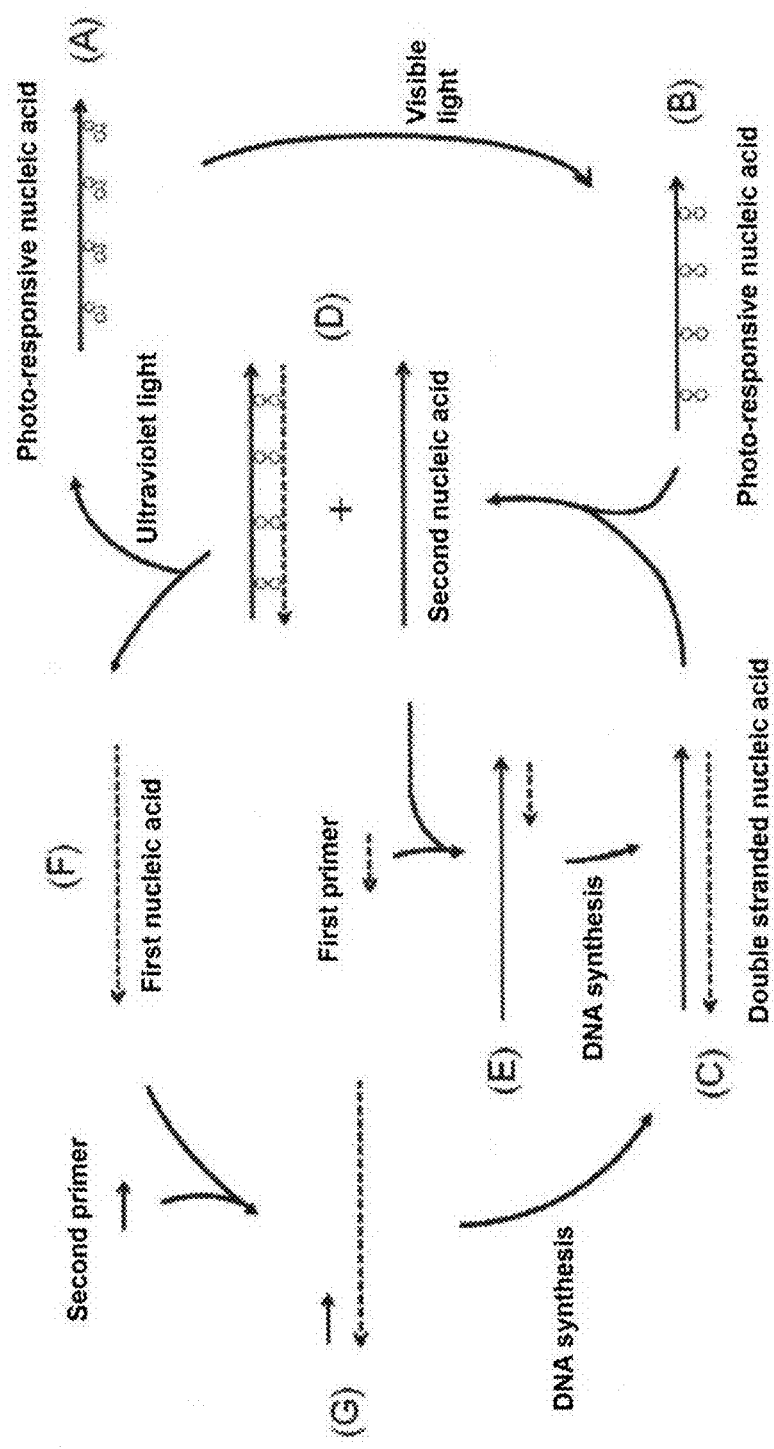
FIG. 4 is a conceptual diagram exemplifying a desirable reaction principle of embodiment 3.
Figure 5:
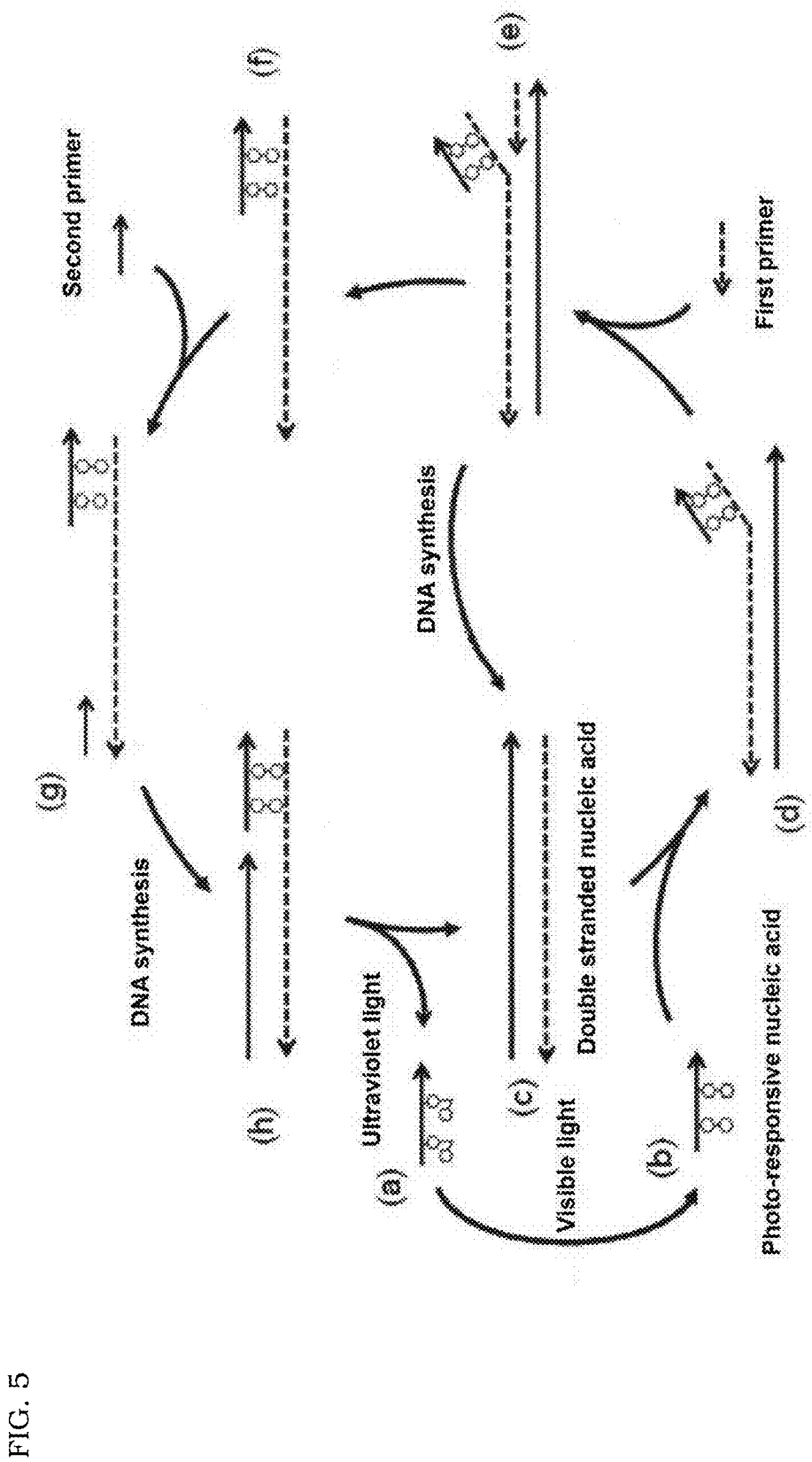
FIG. 5 is a conceptual diagram exemplifying another desirable reaction principle of embodiment 3.

FIGS. 4 and 5 show reaction principles wherein a photo-responsive nucleic acid containing azobenzene attached thereto is used. In FIG. 4, the photo-responsive nucleic acid has the same length as the first nucleic acid and in FIG. 5, the photo-responsive nucleic acid is shorter than the first nucleic acid, with DNA polymerase used being a strand exchange DNA polymerase. In FIGS. 4 and 5, a line with an arrow head represents a nucleic acid strand, wherein the arrow head represents 3' of the nucleic acid strand and the opposite side represents 5'. In FIGS. 4 and 5, a dashed line represents a first nucleic acid in a double stranded nucleic acid and a solid line represents a second nucleic acid.

A series of steps in embodiment 3 are hereinafter described with referring to FIGS. 4 and 5. First, as in embodiment 1, complementary association of a photo-responsive nucleic acid irradiated with light having a first wavelength with a first nucleic acid is allowed to dissociate a second nucleic acid from the first nucleic acid (see (A) to (D) in FIG. 4 and (a) to (d) in FIG. 5). A first primer is then allowed to complementarily associate with the dissociated second nucleic acid (see (D) and (E) in FIG. 4 and (d) and (e) in FIG. 5) and a complementary strand is extended from the first primer with a DNA polymerase (see (E) and (C) in FIG. 4 and (e) and (c) in FIG. 5). Thereby a nucleic acid is amplified with the second nucleic acid being used as a template.

Further in FIG. 4, as in embodiment 2, an irradiation with light having a second wavelength allows the association between the photo-responsive nucleic acid and the first nucleic acid to be dissociated (see (D), (A) and (F) in FIG. 4). A second primer is then allowed to complementarily associate with the dissociated first nucleic acid (see (F) and (G) in FIG. 4) and a complementary strand is extended from the second primer with a DNA polymerase (see (G) and (C) in FIG. 4). In FIG. 5, unlike the process in FIG. 4, a second primer associates with the first nucleic acid to synthesize a complementary strand halfway (see (f), (g) and (h) in FIG. 5) followed by dissociation of the first nucleic acid from the photo-responsive nucleic acid, thereby synthesis of the complementary strand is completed (see (h) and (c) in FIG. 5). However, the present invention is not limited to the process shown in FIG. 5. Even when the photo-responsive nucleic acid is shorter than the first nucleic acid, a complementary strand may be synthesized by association of a second primer to the first nucleic acid after dissociation of the photo-responsive nucleic acid, similarly to the process in FIG. 4. Thereby a nucleic acid is amplified with the first nucleic acid of the double stranded nucleic acid being used as a template. The details for the respective steps are the same as those described for embodiments 1 and 2.

Also in embodiment 3, when the reaction is not terminated, a newly generated double stranded nucleic acid is subjected to the series of the steps described hereinabove, similarly to the double stranded nucleic acid which has originally been present in the reaction system, and the nucleic acid amplification reaction cycle is repeated. As described above, in amplification reaction of embodiment 3, alternate irradiation of lights having different wavelengths allows synthesis of complementary strands of each of a double stranded nucleic acid, resulting in amplification of the double stranded nucleic acid. Namely, by repeating all steps described above, a nucleic acid comprising an extended strand from the first primer complementarily associating with an extended strand from the second primer can be obtained by amplification.

Figure 6:
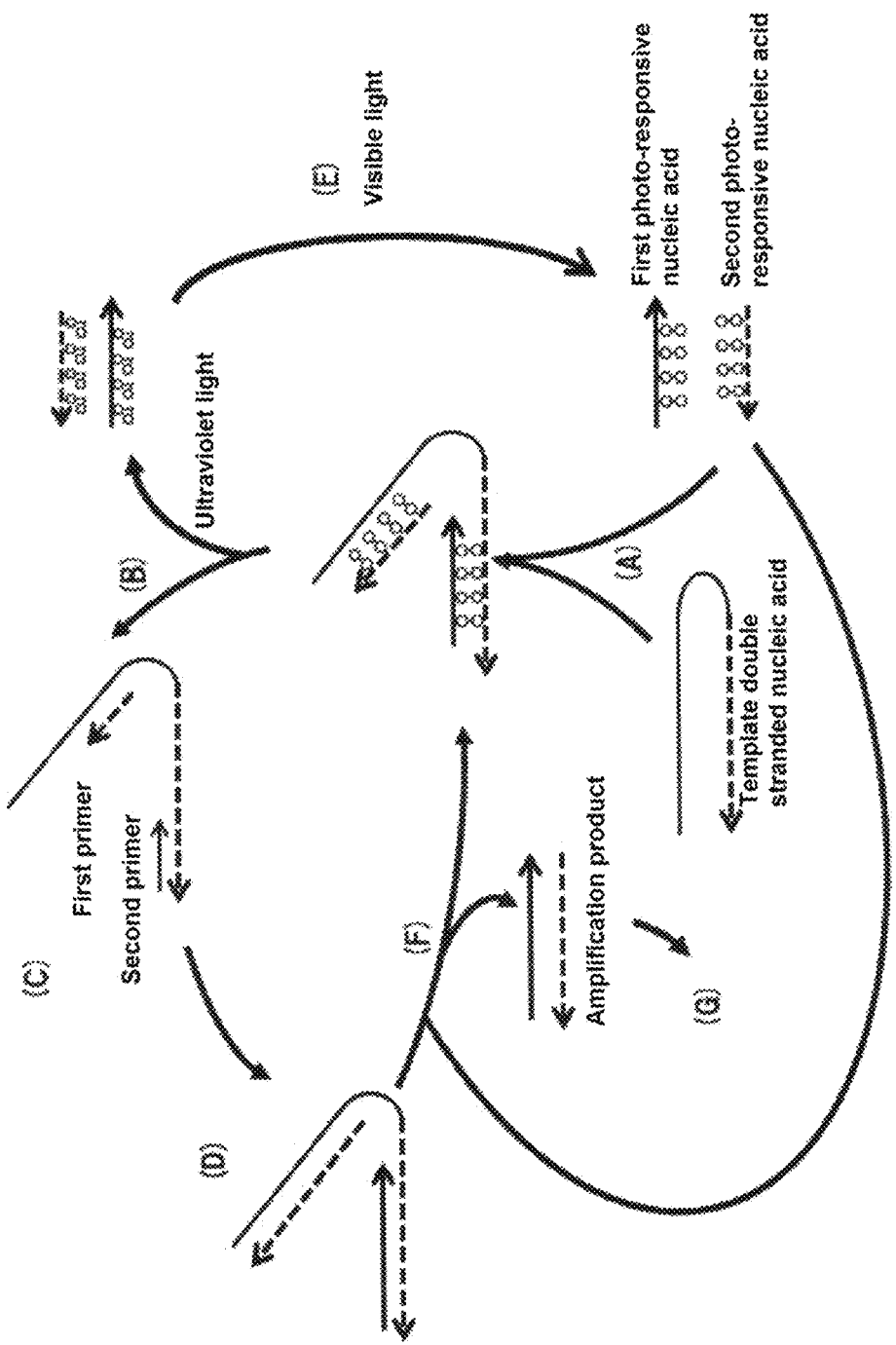
FIG. 6 is a conceptual diagram exemplifying a desirable reaction principle of embodiment 4.
Figure 7:
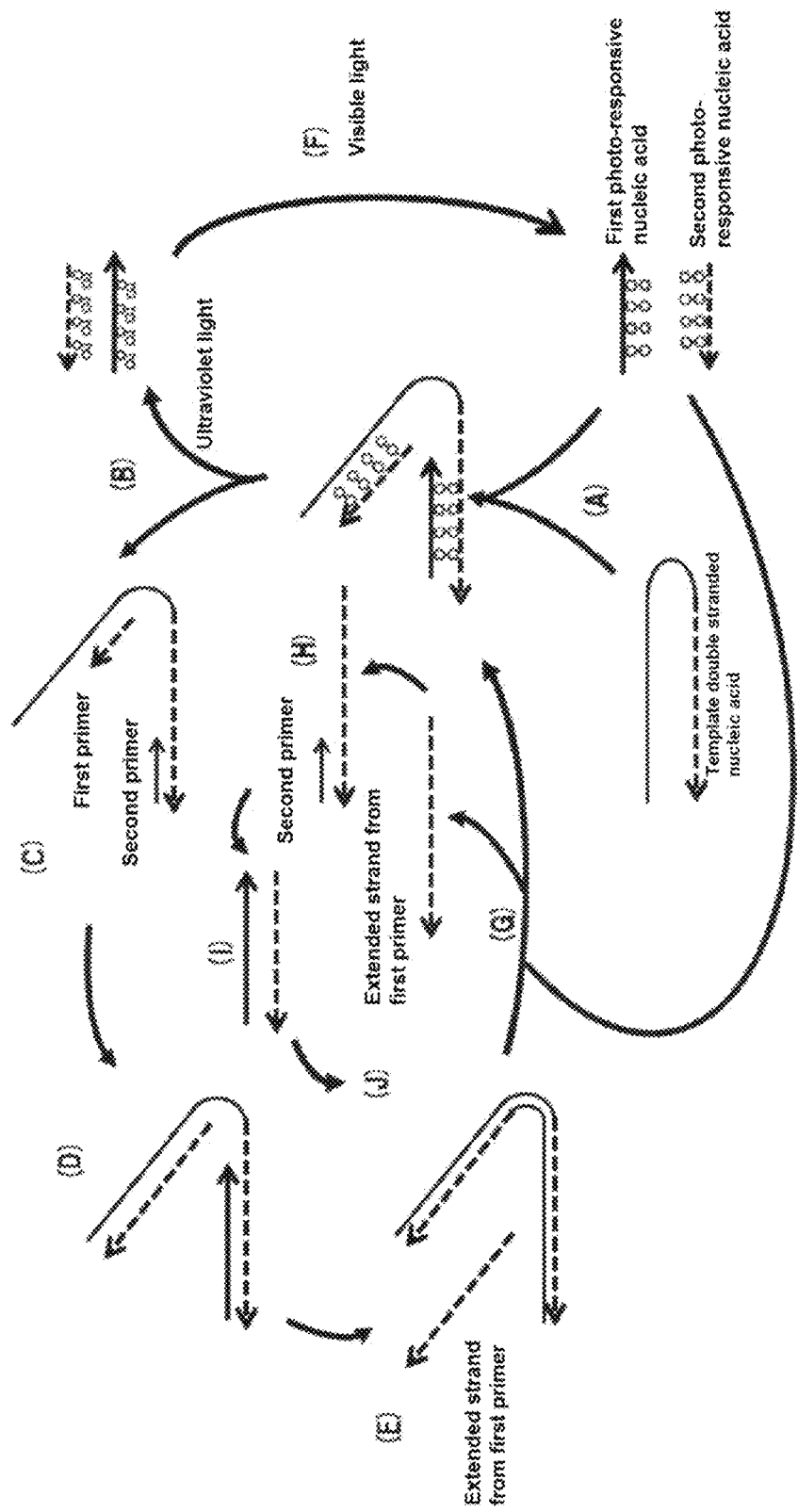
FIG. 7 is a conceptual diagram exemplifying a desirable reaction principle of embodiment 5.

Embodiments (embodiments 4 and 5) wherein a template nucleic acid has a stem-loop structure and two photo-responsive nucleic acids are used are described hereinbelow. See FIGS. 6 and 7 which exemplify desirable reaction principles of embodiments 4 and 5, respectively. In FIGS. 6 and 7, a line with an arrow head represents a nucleic acid strand, wherein the arrow head represents 3' of the nucleic acid strand and the opposite side represents 5'. In FIGS. 6 and 7, a dashed line represents a first nucleic acid in a stem portion of a double stranded nucleic acid and a solid line represents a second nucleic acid.

(A) to (G) as used hereinbelow correspond to (A) to (G) in FIG. 6. A double stranded nucleic acid (also referred to as template nucleic acid) which serves as a template has a stem-loop structure. (A) When the template nucleic acid comes into contact with first and second photo-responsive nucleic acids, a first nucleic acid and a second nucleic acid which are in the stem portion forming a double strand hybridise to the first photo-responsive nucleic acid and the second photo-responsive nucleic acid, respectively. (B) Irradiation of ultraviolet light makes the first and second photo-responsive nucleic acids so as to be incapable of hybridising to nucleic acids, thereby dissociating from the template nucleic acid. (C) First and second primers then hybridise to the parts of the regions with which the photo-responsive nucleic acids have been hybridised. (D) Nucleic acid amplification is carried out by a DNA polymerase from the first and second primers. (E) Photo-responsive nucleic acids which are made to be hybridisable to nucleic acids by irradiation of visible light are then brought into contact with a complex of the template nucleic acid and (F) extended strands from the first and second primers and the photo-responsive nucleic acids bind to the template nucleic acid, thereby extended strands from the first and second primers are dissociated from the template nucleic acid to generate an amplification product. The template nucleic acid to which the photo-responsive nucleic acids are bound is subjected to the cycle of (B) to (F) and the amplification product is generated in (F). Meanwhile, the first and second photo-responsive nucleic acids hybridise to the amplification product, similar amplification as in embodiment 3 is then carried out and the amplification product is generated in (G). In order to avoid formation of a dimer between two photo-responsive nucleic acids after irradiation of visible light, it is preferable that the first photo-responsive nucleic acid and the second photo-responsive nucleic acid are not completely complementary.

(A) to (J) as used hereinbelow correspond to (A) to (J) in FIG. 7. (A) to (D) in embodiment 5 are the same as (A) to (D) in embodiment 4. In the present embodiment, a strand exchange polymerase is used for primer extension reaction. Therefore, (E) extension of a strand from the second primer dissociates a strand extended from the first primer, resulting in formation of a double stranded nucleic acid of an extended strand from the second primer and the template nucleic acid. (F) Photo-responsive nucleic acids which are made to be hybridisable to nucleic acids by irradiation of visible light are then allowed to hybridise with the double stranded nucleic acid of the extended strand from the second primer and the template nucleic acid, (G) thereby the extended strand from the second primer is dissociated as a double stranded nucleic acid having a stem-loop structure and complementary to the template nucleic acid. The stem portion (corresponding to the first nucleic acid and the second nucleic acid) of the double stranded nucleic acid complementary to the template nucleic acid has the same sequence as the stem portion of the template nucleic acid, and the loop portion has the same sequence as the loop portion of the template nucleic acid. As the loop portion is not directly involved in nucleic acid amplification cycles of the present embodiment, the double stranded nucleic acid complementary to the template nucleic acid also serves as a template in the nucleic acid amplification cycles of (A) and afterwards. Meanwhile, (H) the extended strand from the first primer which is dissociated by extension reaction in (E) with the strand exchange DNA polymerase hybridises to the second primer and (I) an extended strand is generated to generate a double stranded nucleic acid. (J) The same amplification as in embodiment 3 is carried out using the double stranded nucleic acid as a template to generate an amplification product. In order to avoid formation of a dimer between two photo-responsive nucleic acids after irradiation of visible light, it is preferable that the first photo-responsive nucleic acid and the second photo-responsive nucleic acid are not completely complementary.

The method according to the present embodiment corresponds to amplification reaction of a double stranded nucleic acid through amplification reaction cycles similar to PCR corresponding to dissociation of a double stranded nucleic acid, association of a primer to a template nucleic acid strand and extension of a primer using a photo-responsive nucleic acid and a primer. Therefore, it is expected that the method according to the present embodiment is applied to various modifications derived from PCR. For example, the method according to the present embodiment can be utilized to in situ nucleic acid amplification for amplifying genes specifically at a region which is irradiated with light.

An amplification product can be detected by electrophoresis and the like. Amplification can also be monitored real time by adding an intercalater such as SYBR® GREEN to a reaction mixture. An amplification product can also be detected by using a probe complementary to a template nucleic acid labelled with two fluorescent substances effecting fluorescence resonance energy transfer (FRET). For example, when two fluorescent substances are proximal, one fluorescent substance quenches fluorescence while the probe is degraded during primer extension with a nucleic acid polymerase having exonuclease activity, generating fluorescence by separation of two fluorescent substances.

In the amplification method described above, two or more photo-responsive nucleic acids may be used. For example, when two photo-responsive nucleic acids are used, a second photo-responsive nucleic acid can be used which binds to a region in a base sequence of a second nucleic acid in a double stranded nucleic acid to be dissociated, the region being different from the region to which a first photo-responsive nucleic acid binds. The region to which the first photo-responsive nucleic acid binds and the region to which the second photo-responsive nucleic acid binds may be distant or adjacent in the second nucleic acid of the double stranded nucleic acid. By using two or more photo-responsive nucleic acids, dissociation can be carried out precisely even when a double stranded nucleic acid has a long sequence.

The present invention is hereinafter described more specifically by way of Examples which do not limit the present invention.

EXAMPLES

Example 1: Verification of Light Irradiation Dependency of Nucleic Acid Amplification Reaction with Photo-Responsive Nucleic Acid In the present Example, it was evaluated whether or not nucleic acid amplification reaction depending on light irradiation can be carried out with a photo-responsive nucleic acid.

(1) Preparation of Nucleic Acids and Reagents

A single stranded DNA containing one 2',6'-dimethylazobenzene attached at every 2 bases was synthesized as a photo-responsive nucleic acid by Tsukuba Oligo Service Co., Ltd. The sequence of the photo-responsive nucleic acid is shown below:

(SEQ ID NO: 1)
5'-CT(Z)TT(Z)AA(Z)GA(Z)AG(Z)GA(Z)GA(Z)TA(Z)TA(Z)CC (Z)TG(Z)AG(Z)TG(Z)AT(Z)CT(Z)AG(Z)TG(Z)TA(Z)CT(Z)

TA-3'

In the above sequence, (Z) represents a site where 2',6'-dimethylazobenzene is inserted. 2',6'-Dimethylazobenzene are attached so as to form side chain moieties of the nucleic acid through D-threoninol integrated into the backbone of the single stranded DNA.

As a template DNA, an unmodified single stranded DNA with the same base sequence of 50 bases as the photo-responsive nucleic acid was synthesized by Life Technologies Japan. The sequence of the single stranded DNA is shown below:

```
                                        (SEQ ID NO: 2)
5'-CTTTAAGAAGGAGATATACCTGAGTGATCTAGTGTACTTAGTATGCT
TCC-3'
```

As a first primer, an unmodified single stranded DNA with 20 bases was synthesized by Life Technologies Japan. As a second primer, a single stranded DNA with 20 bases labelled at the 5'-terminal with Texas Red was synthesized by Japan Bio Services Co., Ltd. The sequences of the primers are shown below:

```
    First primer:
                                        (SEQ ID NO: 3)
    5'-GGAAGCATACTAAGTACACT-3'

Second primer:
                                        (SEQ ID NO: 4)
    5'-Texas Red-CTTTAAGAAGGAGATATACC-3'
```

As a strand-exchange-enhancing substance, a poly(L-lysine)-graft-dextran copolymer (PLL-g-Dex) (molecular weight of PLL: 8000, graft ratio: 90%), which was a cationic block copolymer, was used. DNA polymerase used was Bst DNA polymerase (New England BioLabs). The reaction mixtures used was a diluted 10× ThermoPol buffer (New England BioLabs) enclosed with the polymerase.

(2) Nucleic Acid Amplification

The following four samples were prepared in duplicate.

A sample containing the template DNA (final concentration: 10 nM) and the photo-responsive nucleic acid (final concentration: 500 nM);

A sample containing the template DNA (final concentration: 10 nM) without photo-responsive nucleic acid;

A sample containing the photo-responsive nucleic acid (final concentration: 500 nM) without template DNA; and A sample without template DNA or photo-responsive nucleic acid.

All of the above samples contained 1× ThermoPol buffer solution, the first primer (final concentration: 500 nM), the second primer (final concentration: 500 nM), PLL-g-Dex (final concentration: 78 µM) and Bst DNA polymerase (final concentration: 0.4 units/µL).

The above-prepared samples (20 µL each) were distributed into 0.2-mL tubes which were then sealed with an adhesive tape (Thermo Scientific). The tubes were heated for 10 minutes at 60° C. on a Thermal Cycler PC320 (Astec Co., Ltd.). By this procedure, a strand complementary to the template DNA was synthesized by the first primer, resulting in synthesis of a double stranded DNA which was sought to be amplified in the present Example.

One of each above-prepared samples was incubated for 20 minutes on the thermal cycler heated to 60° C. The remaining samples were subjected to the following procedures i) to iv) five times:

i) A tube was placed in a stainless tube rack heated to 60° C. and irradiated with light (wavelength: 470 to 495 nm) which was emitted from a light source of a mercury lamp (ultra-high pressure UV lamp USH-1030L, Olympus Corporation) and passed through a visible light filter (U-MNIBA3, Olympus Corporation), for 1 minute from the top of the tube.

ii) The tube was placed back to the thermal cycler heated to 60° C. and incubated for 1 minute.

iii) The tube was placed in a stainless tube rack heated to 60° C. and irradiated with light (wavelength 330 to 385 nm) which was emitted from a light source of a mercury lamp (ultra-high pressure UV lamp USH-1030L, Olympus Corporation) and passed through an ultraviolet light filter (U-MWU2, Olympus Corporation), for 1 minute from the top of the tube.

iv) The tube was placed back to the thermal cycler heated to 60° C. and incubated for 1 minute.

Figure 8:
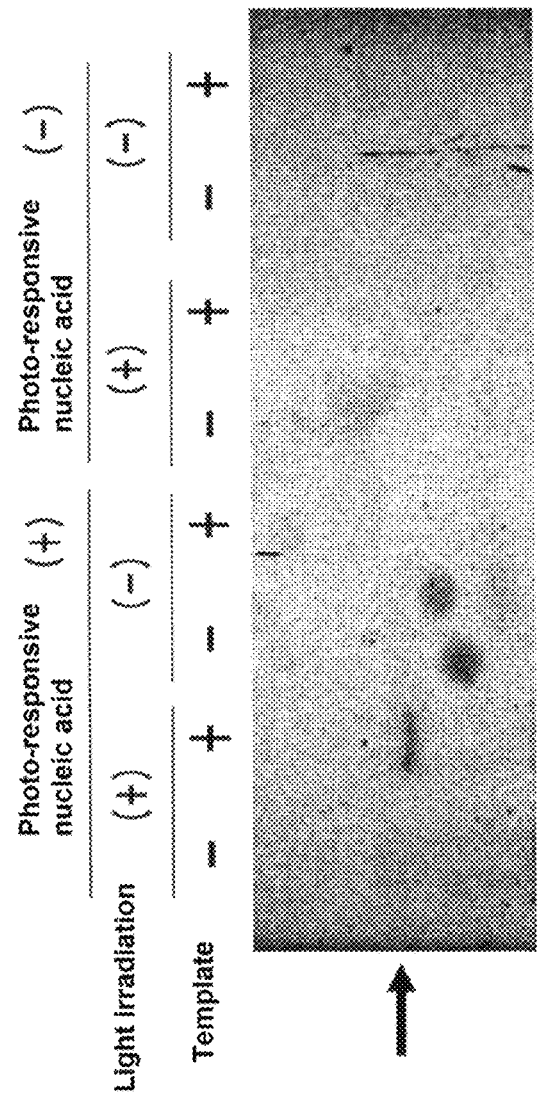
FIG. 8 is a fluorescence image showing amplification of a double stranded nucleic acid in a light irradiation-dependent manner.

A portion of the sample (10 µL) was taken out from each tube and added with 1 M poly(vinyl sulphate) potassium salt to the final concentration of 0.1 M. The mixture was left to stand at 4° C. for 90 minutes. The resulting sample was further added with an equivalent amount of a formamide loading solution (95% formamide, NaOH, 2% bromophenol blue) and heated at 95° C. for 5 minutes to give a sample for electrophoresis. The obtained sample was subjected to electrophoresis on a 20% acrylamide gel containing 4% urea (300 V, 30 minutes). A fluorescent image of the gel after electrophoresis was collected on a Molecular Imager (Bio-Rad). The obtained image is shown in FIG. 8. The resulting fluorescent image was converted to tif files and the intensity of fluorescent signals from the amplification products derived from the second primer was converted to the numerical values with the Image J software (available from the website of the National Institute of Health (NIH)).

(3) Results

As apparent from FIG. 8, a signal indicating amplification of DNA was not detected under the conditions of absence the photo-responsive nucleic acid or absence light irradiation even in the presence of the template DNA. On the other hand, it was confirmed that DNA synthesis specific to the template DNA occurred in the presence of the photo-responsive nucleic acid with light irradiation (see the band indicated with the arrow in FIG. 8). Therefore, it was demonstrated that light-irradiation-dependent nucleic acid amplification reaction can be carried out.

Example 2: Verification of Dependency of Nucleic Acid Amplification Reaction with a Photo-responsive Nucleic Acid on the Number of Light Irradiation Cycles In the present Example, it was verified whether or not the nucleic acid amplification reaction with a photo-responsive nucleic acid progresses in a manner dependent to the number of light irradiation cycles.

(1) Preparation of Nucleic Acids and Reagents

In the present Example, the same photo-responsive nucleic acid, template DNA, first primer and second primer as Example 1 were used. Similarly to Example 1, a strand-exchange-enhancing substance, PLL-g-Dex (molecular weight of PLL: 8000, graft ratio: 90%) and a DNA polymerase, Bst DNA polymerase (New England BioLabs) were used. The reaction mixtures used was a diluted 10× ThermoPol buffer (New England BioLabs) enclosed with the polymerase.

(2) Nucleic Acid Amplification

Four samples containing 1× ThermoPol buffer solution, the template DNA (final concentration: 10 nM), the photo-responsive nucleic acid (final concentration: 500 nM), the first primer (final concentration: 500 nM), the second primer (final concentration: 500 nM), PLL-g-Dex (final concentration: 78 µM) and Bst DNA polymerase (final concentration: 0.4 units/µL) were prepared.

The above-prepared samples (20 µL each) were distributed into 0.2-mL tubes which were then sealed with an adhesive tape (Thermo Scientific). The tubes were heated for 10 minutes at 60° C. on a Thermal Cycler PC320 (Astec Co., Ltd.). By this procedure, a strand complementary to the template DNA was synthesized by the first primer, resulting in synthesis of a double stranded DNA which was sought to be amplified in the present Example.

Figure 9:
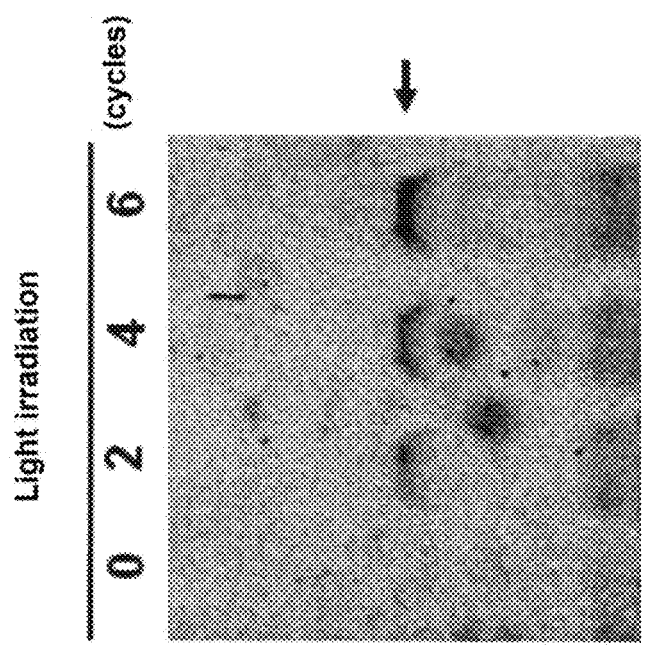
FIG. 9 is a fluorescence image showing amplification of a double stranded nucleic acid in a manner depending on the number of light irradiation cycles.

Each of four samples was subjected to the procedures i) to iv) described in Example 1 zero, 2, 4 or 6 times. Thereafter, a sample for electrophoresis was prepared from each sample by the same manner as in Example 1 and the obtained sample was subjected to electrophoresis on a 20% acrylamide gel containing 4% urea (300 V, 30 minutes). A fluorescent image of the gel after electrophoresis was collected on a Molecular Imager (Bio-Rad). The obtained image is shown in FIG. 9. The resulting fluorescent image was converted to tif files and the intensity of fluorescent signals from the amplification products derived from the second primer was converted to the numerical values with the Image J software to generate a graph which is shown in FIG. 10.

Figure 10:
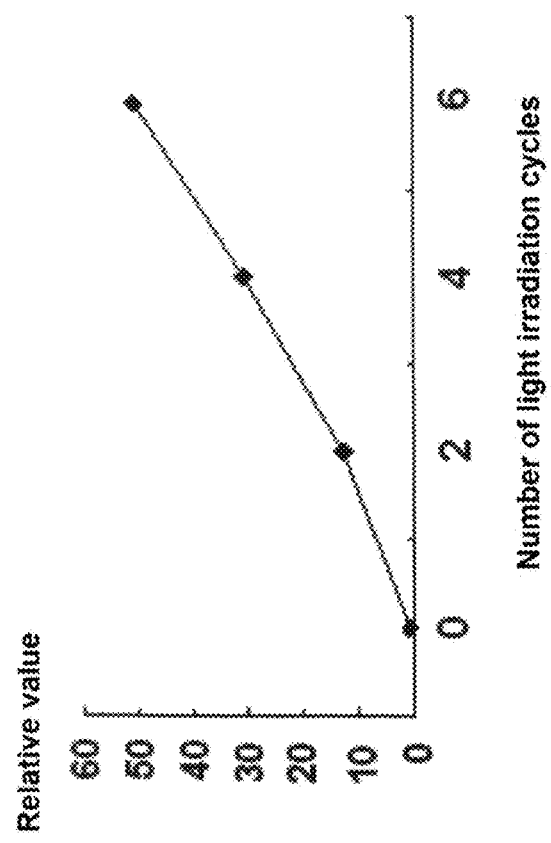
FIG. 10 is a graph showing amplification of a double stranded nucleic acid in a manner depending on the number of light irradiation cycles.

As shown in FIGS. 9 and 10, no signal was detected when no light irradiation cycle was carried out. However, it was confirmed that with an increase in the number of light irradiation cycles, the signal intensity derived from the synthesized double stranded DNA was increased. Thus it was demonstrated that a cycle of amplification reaction was repeated by alternately irradiating light having two different wavelengths and the amount of amplified DNA can be increased by an increase in the number of light irradiation cycles.

What is claimed is:

1. A method for amplifying a nucleic acid, comprising the steps of:
- irradiating a photo-responsive nucleic acid with light having a first wavelength to make the photo-responsive nucleic acid capable of associating with a first nucleic acid of a double stranded nucleic acid, wherein the double stranded nucleic acid comprises the first nucleic acid and a second nucleic acid, wherein the first nucleic acid is a single strand, and the second nucleic acid is a single strand and comprises a nucleotide sequence complementary to the first nucleic acid;
- allowing complementary association of the photo-responsive nucleic acid with the first nucleic acid to dissociate the second nucleic acid from the first nucleic acid;
- allowing complementary association of a first primer to the dissociated second nucleic acid; and
- extending a complementary strand from the first primer with a DNA polymerase,
- wherein the method is carried out under a substantially isothermal condition, and
- wherein all the steps are repeated to amplify the nucleic acid.

2. The method according to claim 1, wherein the photo-responsive nucleic acid comprises at least one selected from the group consisting of azobenzene and a derivative thereof.

3. The method according to claim 2, wherein the photo-responsive nucleic acid is made capable of associating with the first nucleic acid by transforming at least one selected from the group consisting of azobenzene and a derivative thereof from a cis form to a trans form by irradiation with light having the first wavelength.

4. The method according to claim 2, wherein the derivative of azobenzene is dimethylazobenzene.

5. The method according to claim 1, wherein the method is carried out in the presence of a strand-exchange-enhancing substance.

6. The method according to claim 5, wherein the strand-exchange-enhancing substance is at least one selected from the group consisting of a cationic homopolymer and a cationic copolymer.

7. The method according to claim 6, wherein the cationic copolymer is a poly(L-lysine)-graft-dextran copolymer (PLL-g-Dex).

8. The method according to claim 1, wherein the DNA polymerase is a strand exchange DNA polymerase.

9. A method for amplifying a nucleic acid, comprising the steps of:
- irradiating a photo-responsive nucleic acid with light having a first wavelength to make the photo-responsive nucleic acid capable of associating with a first nucleic acid of a double stranded nucleic acid, wherein the double stranded nucleic acid comprises the first nucleic acid and a second nucleic acid, wherein the first nucleic acid is a single strand, and the second nucleic acid is a single strand and comprises a nucleotide sequence complementary to the first nucleic acid;
- allowing complementary association of the photo-responsive nucleic acid with the first nucleic acid to dissociate the second nucleic acid from the first nucleic acid;
- irradiating the photo-responsive nucleic acid with light having a second wavelength that is different from the first wavelength to make the photo-responsive nucleic acid incapable of associating with the first nucleic acid;
- allowing dissociation of the photo-responsive nucleic acid from the first nucleic acid;
- allowing complementary association of a primer to the dissociated first nucleic acid; and
- extending a complementary strand from the primer with a DNA polymerase,
- wherein the method is carried out under a substantially isothermal condition.

10. The method according to claim 9, wherein the photo-responsive nucleic acid comprises at least one selected from the group consisting of azobenzene and a derivative thereof.

11. The method according to claim 10, wherein the photo-responsive nucleic acid is made capable of associating with the first nucleic acid by transforming at least one selected from the group consisting of azobenzene and a derivative thereof from a cis form to a trans form by irradiation with light having the first wavelength.

12. The method according to claim 10, wherein the photo-responsive nucleic acid is made incapable of associating with the first nucleic acid by transforming at least one selected from the group consisting of azobenzene and a derivative thereof from a trans form to a cis form by irradiation with light having the second wavelength.

13. The method according to claim 10, wherein the derivative of azobenzene is dimethylazobenzene.

14. The method according to claim 9, wherein all the steps are repeated to amplify the nucleic acid.

15. The method according to claim 9, wherein the method is carried out in the presence of a strand-exchange-enhancing substance.

16. The method according to claim 15, wherein the strand-exchange-enhancing substance is at least one selected from the group consisting of a cationic homopolymer and a cationic copolymer.

17. The method according to claim 16, wherein the cationic copolymer is a poly(L-lysine)-graft-dextran copolymer (PLL-g-Dex).

18. A method for amplifying a nucleic acid, comprising the steps of:
- irradiating a photo-responsive nucleic acid with light having a first wavelength to make the photo-responsive nucleic acid capable of associating with a first nucleic acid of a double stranded nucleic acid, wherein the double stranded nucleic acid comprises the first nucleic acid and a second nucleic acid, wherein the first nucleic acid is a single strand, and the second nucleic acid is a single strand and comprises a nucleotide sequence complementary to the first nucleic acid;

allowing complementary association of the photo-responsive nucleic acid with the first nucleic acid to dissociate the second nucleic acid from the first nucleic acid;

allowing complementary association of a first primer to the dissociated second nucleic acid;

extending a complementary strand from the first primer with a DNA polymerase, irradiating the photo-responsive nucleic acid with light having a second wavelength that is different from the first wavelength to make the photo-responsive nucleic acid incapable of associating with the first nucleic acid;

allowing dissociation of the photo-responsive nucleic acid from the first nucleic acid;

allowing complementary association of a second primer to the dissociated first nucleic acid; and extending a complementary strand from the second primer with a DNA polymerase, wherein the method is carried out under a substantially isothermal condition.

19. The method according to claim 18, wherein all the steps are repeated, thereby amplifying a nucleic acid comprising an extended strand from the first primer complementarily associated with an extended strand from the second primer.

* * * * *

```
                        SEQUENCE LISTING

<160> NUMBER OF SEQ ID NOS: 4

<210> SEQ ID NO 1
<211> LENGTH: 40
<212> TYPE: DNA
<213> ORGANISM: Artificial Sequence
<220> FEATURE:
<223> OTHER INFORMATION: photo-reactive oligonucleotide
<220> FEATURE:
<221> NAME/KEY: misc_feature
<222> LOCATION: (2)..(3)
<223> OTHER INFORMATION: Dimethyl-azobenzene-conjugated D-threoninol is
      inserted between positions 2 and 3
<220> FEATURE:
<221> NAME/KEY: misc_feature
<222> LOCATION: (4)..(5)
<223> OTHER INFORMATION: Dimethylazobenzene-conjugated D-threoninol is
      inserted between positions 4 and 5
<220> FEATURE:
<221> NAME/KEY: misc_feature
<222> LOCATION: (6)..(7)
<223> OTHER INFORMATION: Dimethylazobenzene-conjugated D-threoninol is
      inserted between positions 6 and 7
<220> FEATURE:
<221> NAME/KEY: misc_feature
<222> LOCATION: (8)..(9)
<223> OTHER INFORMATION: Dimethylazobenzene-conjugated D-threoninol is
      inserted between positions 8 and 9
<220> FEATURE:
<221> NAME/KEY: misc_feature
<222> LOCATION: (10)..(11)
<223> OTHER INFORMATION: Dimethylazobenzene-conjugated D-threoninol is
      inserted between positions 10 and 11
<220> FEATURE:
<221> NAME/KEY: misc_feature
<222> LOCATION: (12)..(13)
<223> OTHER INFORMATION: Dimethylazobenzene-conjugated D-threoninol is
      inserted between positions 12 and 13
<220> FEATURE:
<221> NAME/KEY: misc_feature
<222> LOCATION: (14)..(15)
<223> OTHER INFORMATION: Dimethylazobenzene-conjugated D-threoninol is
      inserted between positions 14 and 15
<220> FEATURE:
<221> NAME/KEY: misc_feature
<222> LOCATION: (16)..(17)
<223> OTHER INFORMATION: Dimethylazobenzene-conjugated D-threoninol is
      inserted between positions 16 and 17
<220> FEATURE:
<221> NAME/KEY: misc_feature
<222> LOCATION: (18)..(19)
<223> OTHER INFORMATION: Dimethylazobenzene-conjugated D-threoninol is
      inserted between positions 18 and 19
<220> FEATURE:
```

```
<221> NAME/KEY: misc_feature
<222> LOCATION: (20)..(21)
<223> OTHER INFORMATION: Dimethylazobenzene-conjugated D-threoninol is
      inserted between positions 20 and 21
<220> FEATURE:
<221> NAME/KEY: misc_feature
<222> LOCATION: (22)..(23)
<223> OTHER INFORMATION: Dimethylazobenzene-conjugated D-threoninol is
      inserted between positions 22 and 23
<220> FEATURE:
<221> NAME/KEY: misc_feature
<222> LOCATION: (24)..(25)
<223> OTHER INFORMATION: Dimethylazobenzene-conjugated D-threoninol is
      inserted between positions 24 and 25
<220> FEATURE:
<221> NAME/KEY: misc_feature
<222> LOCATION: (26)..(27)
<223> OTHER INFORMATION: Dimethylazobenzene-conjugated D-threoninol is
      inserted between positions 26 and 27
<220> FEATURE:
<221> NAME/KEY: misc_feature
<222> LOCATION: (28)..(29)
<223> OTHER INFORMATION: Dimethylazobenzene-conjugated D-threoninol is
      inserted between positions 28 and 29
<220> FEATURE:
<221> NAME/KEY: misc_feature
<222> LOCATION: (30)..(31)
<223> OTHER INFORMATION: Dimethylazobenzene-conjugated D-threoninol is
      inserted between positions 30 and 31
<220> FEATURE:
<221> NAME/KEY: misc_feature
<222> LOCATION: (32)..(33)
<223> OTHER INFORMATION: Dimethylazobenzene-conjugated D-threoninol is
      inserted between positions 32 and 33
<220> FEATURE:
<221> NAME/KEY: misc_feature
<222> LOCATION: (34)..(35)
<223> OTHER INFORMATION: Dimethylazobenzene-conjugated D-threoninol is
      inserted between positions 34 and 35
<220> FEATURE:
<221> NAME/KEY: misc_feature
<222> LOCATION: (36)..(37)
<223> OTHER INFORMATION: Dimethylazobenzene-conjugated D-threoninol is
      inserted between positions 36 and 37
<220> FEATURE:
<221> NAME/KEY: misc_feature
<222> LOCATION: (38)..(39)
<223> OTHER INFORMATION: Dimethylazobenzene-conjugated D-threoninol is
      inserted between positions 38 and 39

<400> SEQUENCE: 1
ctttaagaag gagatatacc tgagtgatct agtgtactta                           40

<210> SEQ ID NO 2
<211> LENGTH: 50
<212> TYPE: DNA
<213> ORGANISM: Artificial Sequence
<220> FEATURE:
<223> OTHER INFORMATION: template DNA

<400> SEQUENCE: 2
ctttaagaag gagatatacc tgagtgatct agtgtactta gtatgcttcc                50

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggaagcatac taagtacact                                                 20
```

```
<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ctttaagaag gagatatacc                                                      20
```